United States Patent [19]

Woolard

[11] Patent Number: 4,956,006

[45] Date of Patent: Sep. 11, 1990

[54] SUBSTITUTED 1-PHENYL PYRROLIDONES AND THEIR USE AS HERBICIDES

[75] Inventor: Frank X. Woolard, Richmond, Calif.

[73] Assignee: ICI Americas Inc., Wilmington, Del.

[21] Appl. No.: 291,081

[22] Filed: Dec. 27, 1988

[51] Int. Cl.$^5$ .................. C07D 207/26; C07D 403/06; A01N 43/36

[52] U.S. Cl. .............................. 71/95; 71/94; 548/544; 548/551; 548/530

[58] Field of Search .............. 548/543, 544, 551, 530; 71/95, 94; 546/281

[56] References Cited

U.S. PATENT DOCUMENTS

| | | | |
|---|---|---|---|
| 4,069,038 | 1/1978 | Teach | 548/543 |
| 4,087,270 | 5/1978 | Schneider et al. | 548/543 |
| 4,110,105 | 8/1978 | Teach | 71/95 |
| 4,208,202 | 1/1980 | Tobler et al. | 548/543 |
| 4,210,589 | 7/1980 | Teach | 548/543 |
| 4,505,737 | 3/1985 | Thiele et al. | 548/543 |
| 4,645,843 | 2/1987 | Broadhurst et al. | 548/543 |

FOREIGN PATENT DOCUMENTS 728663  12/1962  Canada .................. 548/543

*Primary Examiner*—David B. Springer
*Attorney, Agent, or Firm*—Michael J. Bradley

[57] ABSTRACT

Substituted 1-phenyl pyrrolidones of the formula

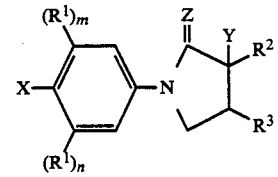

in which $R^1$ is halogen, trifluoromethyl, cyano, $CH_3$, $CF_2CHF_2$, $OCF_2CHF_2$, $OCHF_2$, $OCF_3$, $SCH_3$, $S(O)CH_3$, $SO_2CH_3$, methoxyiminomethyl, methoxyimino-1-ethyl, benzoyloxyiminomethyl, benzoyloxyimino-1-ethyl, pyridyloxy, or pyridyloxy substituted with halogen and/or trifluoromethyl; $R^2$ halogen, cyano, carboxy, carbalkoxy or carbalkoxy substituted with halogen, trifluoromethyl or phenyl; $R^3$ is $C_1$–$C_4$ alkyl or $C_2$–$C_4$ alkenyl; X is H or halogen; Y is H or halogen; Z is O or S; and m and n are zero or 1; are useful as herbicidal agents.

54 Claims, No Drawings

SUBSTITUTED 1-PHENYL PYRROLIDONES AND THEIR USE AS HERBICIDES

BACKGROUND AND SUMMARY OF THE INVENTION

This invention relates to substituted pyrrolidones and to their use in herbicidal formulations. In particular, this invention relates to substituted 1-phenyl pyrrolidones of the formula

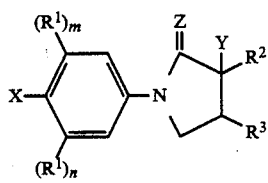

in which:
R$^1$ is a member selected from the group consisting of halogen, trifluoromethyl, cyano, CH$_3$, CF$_2$CHF$_2$, OCF$_2$CHF$_2$, OCHF$_2$, OCF$_3$, SCH$_3$, S(O)CH$_3$, SO$_2$CH$_3$, methoxyiminomethyl, methoxyimino-1-ethyl, benzoyloxyiminomethyl, benzoyloxyimino-1-ethyl, pyridyloxy, and pyridyloxy substituted with one or more members of the group consisting of halogen and trifluoromethyl;
R$^2$ is a member selected from the group consisting of halogen, cyano, carboxy, carbalkoxy containing an alkyl group of 1 to 8 carbon atoms, and carbalkoxy containing an alkyl group of 1 to 8 carbon atoms substituted with a member selected from the group consisting of halogen, trifluoromethyl and phenyl;
R$^3$ selected from the group consisting of C$_1$-C$_4$ alkyl and C$_2$-C$_4$ alkenyl;
X is a member selected from the group consisting of H and halogen;
Y is a member selected from the group consisting of H and halogen;
Z is a member selected from the group consisting of O and S; and
m and n are independently zero or 1.

The compounds of the present invention, as will be seen from the description and test data which follows, have utility as both pre-emergence and post-emergence herbicides, against a wide range of plant species. The compounds are of particular interest when used in pre-emergence application.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn, and dwarfing. The term "herbicidally effective amount" is used to denote any amount which achieves such control or modification when applied to the undesired plants themselves or to the area in which these plants are growing. The term "plants" is intended to include germinant seeds, emerging seedlings and established vegetation, including both roots and above-ground portions.

DETAILED DESCRIPTION OF THE INVENTION AND PREFERRED EMBODIMENTS

Within the scope of the above formula, certain embodiments are preferred, as follows.

R$^1$ is preferably halogen, trifluoromethyl, cyano or pyridyloxy substituted with halogen and/or trifluoromethyl. Preferred pyridyloxy groups are pyrid-2-yloxy. In further preferred embodiments, R$^1$ is chloro, trifluoromethyl, cyano or pyrid-2-yloxy substituted with halogen, particularly chloro, and/or trifluoromethyl. In the most preferred embodiments, R$^1$ is trifluoromethyl or cyano.

X is preferably H or fluoro, and most preferably H.

The values of m and n are preferably m=1 and n=zero.

R$^2$ is preferably halogen, carboxy or carbalkoxy in which the alkyl group contains 1 to 4 carbon atoms. In more preferred embodiments, R$^2$ is chloro, carboxy and carbethoxy.

R$^3$ is preferably C$_1$-C$_4$ alkyl. Particularly preferred R$^3$ groups are ethyl and vinyl, with ethyl being the most preferred.

Y is preferably H or chloro, with H the most preferred.

Z is preferably O.

The term "carboxy" is used herein to designate the —COOH group, and the term "carbalkoxy" (used interchangeably with "carboalkoxy") is used to designate an alkyl ester of this group, i.e., —COOR where R is an alkyl group of the designated number of carbon atoms. The term "carbethoxy" or "carboethoxy" for example designates —COOC$_2$H$_5$. The term "alkyl" and all groups containing alkyl portions are intended to include both straight-chain, branched-chain and cyclic groups. Examples are methyl, ethyl, n-propyl, isopropyl, cyclopropyl, n-butyl, t-butyl, 2-methyl-n-butyl, n-hexyl, cyclohexyl, and cyclopropylmethyl.

It will be noted that the generic formula representing the substituted 1-phenyl pyrrolidones of the present invention indicates two chiral centers, one at the 3-position and the other at the 4-position of the pyrrolidone ring. The specific compounds disclosed herein each represent a mixture of enantiomers at both chiral centers, unless otherwise indicated. Herbicidal activity for the mixture is an indication of herbicidal activity for each individual enantiomer. In certain cases, however, one enantiomer will have a greater herbicidal activity than the other enantiomer for a given chiral center. For example, for those compounds where Y is H, the enantiomers having the greatest activity will generally be those in which the R$^2$ and R$^3$ groups are trans to each other.

Compounds where R$^1$ is meta-trifluoromethyl or metacyano, Y is H, R$^2$ is halo (particularly chloro), and R$^3$ is ethyl are of particular interest for their tolerance to cotton and wheat crops, tho latter particularly under growing conditions commonly in use in Europe.

The compounds of this invention are prepared by a step-wise sequence of transformations that begins with the preparation of N-alkyl anilines variously substituted on the aromatic ring. These N-alkyl anilines are prepared either by
  (a) the alkylation of an acetanilide with an alkyl halide and strong base such as sodium hydride, followed by hydrolysis, or (b) the reaction of an aniline with an aliphatic aldehyde in the presence of a water scavenger such as titanium tetrachloride, followed by reduction of the product imine with sodium borohydride.

The N-alkylanilines are then treated with ethyl malonyl chloride in a non-polar solvent such as chloroform, methylene chloride, toluene or benzene in the presence of an organic base such as triethyl amine or pyridine while maintaining the temperature between 5° C. and 20° C. The resulting ethyl N-aryl-N-alkylmalonate monoamides are then combined in a polar organic solvent, for example acetonitrile, with equivalent amounts of p-toluenesulfonyl azide and an organic base such as triethylamine to form ethyl N-aryl-N-alkyldiazomalonate monoamides. The dropwise addition of these compounds to a refluxing suspension of rhodium (II) acetate dimer in benzene decomposes the diazo group to nitrogen gas and a carbene species which immediately undergoes intramolecular reaction to form a 3-carboethoxy-4-alkylpyrrolidone ring.

Subsequent treatment of these systems with a chlorinating agent such as sulfuryl chloride in a non-polar aprotic solvent such as methylene chloride adds a chlorine to the 3-position of the pyrrolidone ring. Hydrolysis of the ester group with either potassium or sodium hydroxide in water/ethanol mixtures followed by acidification with a mineral acid provides 3-chloro-3-carboxypyrrolidones which, upon heating neat to 140°–170° C. liberate carbon dioxide to form the desired product.

The following are examples of compounds which have been synthesized by the procedures described above. These examples are offered strictly for purposes of illustration, and are intended neither to limit nor to define the invention in any manner.

EXAMPLE 1

This example illustrates the preparation of 1-(3-trifluoromethylphenyl)-3-chloro-4-ethyl-2-pyrrolidone in which, according to the above formula, m is 1, n is zero, $R^1$ is $CF_3$, $R^2$ is Cl, $R^3$ is $C_2H_5$, X and Y are both H and Z is O. This compound is represented in Table I below as Compound No. 4.

The synthesis began with the preparation of m-(N-n-butyl)aminobenzotrifluoride, as follows. A two-liter three-necked round-bottomed flask equipped with a mechanical stirrer, thermometer, and pressure equalizing addition funnel carrying a nitrogen bubbler was charged with 64.46 g (0.40 mol) of m-aminobenzotrifluoride. 101.19 g (1.00 mol) of triethylamine, and 200 mL of dry ether. The solution was stirred and cooled to 3° C. by immersing the flask in an external ice bath. Freshly distilled butyraldehyde (36.05 g 0.50 mol) in 200 mL of ether was then added all at once. A solution of titanium tetrachloride in 35 mL of dry benzene was then added dropwise at such a rate that the temperature did not rise above 5° C. When the addition was complete an additional 10 mL of butyraldehyde were added and the mixture filtered through diatomaceous earth to remove the precipitated titanium dioxide. The ether solvent was then removed in vacuo and the resulting yellow oil dissolved in 600 mL of absolute ethanol. The solution was stirred magnetically and 15.13 g (0.40 mol) of sodium borohydride added batchwise in portions of approximately 1 g each at such a rate that the foaming was controlled. One-half hour after the last addition, gas chromatography (GC) analysis showed the reaction to be complete.

After removal of the bulk of the ethanol in vacuo 250 mL of water was added to the residue and the pH adjusted to 8 with concentrated HCl. The oily aqueous mixture was then extracted with three 100-mL portions of ethyl acetate. The extracts were combined, dried ($MgSO_4$), and the solvent removed in vacuo to give a light yellow oil that was distilled under reduced pressure to yield 54.05 g (62%) of m-(N-n-butyl)aminobenzotrifluoride as a colorless oil; boiling point 62.5–63.5° C. at 0.050 mm Hg.

As an alternative route to the same intermediate. N-(3-trifluoromethylphenyl)-N-butyldichloroacetanilide was formed and converted as follows. A one-liter round-bottomed flask equipped with a mechanical stirrer, heating mantle, pressure equalizing addition funnel, and reflux condenser carrying a nitrogen bubbler was charged with 5.23 g (0.22 mol) of sodium hydride and 100 mL of tetrahydrofuran (THF). freshly distilled from sodium/benzophenone. The suspension was stirred, and a solution of 54.41 g (0.20 mol) of 3-trifluoromethyl-dichloroacetanilide in 100 mL of THF was added dropwise with stirring at such a rate that hydrogen evolution was controlled. When the addition was complete, 27.41 g (0.20 mol) of n-butyl bromide were added all at once and the solution was heated to reflux for 48 hours. The solution was then allowed to cool, and 50 mL of 3% aqueous HCl cautiously added.

The THF was then removed under reduced pressure and the crude N-(3-trifluoromethyl)phenyl-N-butyldichloroacetanilide, weighing 58.15 g was dissolved in 150 mL of absolute ethanol. A solution of 6.8 g of sodium hydroxide in 10 mL of water was added all at once. The solution was stirred at room temperature for 18 hours at which time the ethanol was removed in vacuo. The resulting semi-solid was partitioned between 100 mL of water and 100 mL of ethyl acetate. The layers were separated and the aqueous phase extracted with two 50-mL portions of ethyl acetate. The organic layers were combined, dried ($MgSO_4$) and the solvent removed under reduced pressure. Vacuum distillation of the residual oil provided 14.50 g (33%) of m-(N-n-butyl)aminobenzotrifluoride as a colorless oil; boiling point 62.5°–63.5° C. at 0.05 mm Hg.

Conversion to ethyl N-(3-trifluoromethylphenyl)-N-butylmalonate monoamide then proceeded as follows. To a 300-mL three-necked round-bottomed flask equipped with a magnetic stirrer, thermometer, and pressure equalizing addition funnel carrying a nitrogen bubbler was added 12.92 g (59.5 mmol) of the aminobenzotrifluoride. 100 mL of methylene chloride, and 4.82 g (61.0 mmol) of pyridine. The solution was stirred, cooled to 5° C. with an external ice bath, and 9.18 g (61.0 mmol) of ethyl malonylchloride in 25 mL of methylene chloride added at such a rate that the temperature did not rise above 10° C. When the addition was complete the stirring was continued for one-half hour. The reaction mixture was then washed with two 150-mL portions of 3% aqueous HCl, followed by 100 mL of water, then dried ($MgSO_4$), and the solvent removed in vacuo to give 18.56 g (94%) of the monoamide as a tan-yellow oil.

This was then converted to ethyl N-(3-trifluoromethylphenyl)-N-butyldiazomalonate monoamide as follows. A 100-mL three-necked round-bottomed flask equipped with a magnetic stirrer, thermometer, and pressure equalizing addition funnel carrying a nitrogen bubbler was charged with 10.00 g (30.2 mmol) of the product of the last step. 40 mL of acetonitrile, and 3.05 g (30.2 mmol) of triethylamine. The solution was stirred and a solution of 5.96 g (30.2 mmol) of p-toluenesulfonylazide added dropwise over 15 minutes. During this time there was a three-degree exotherm (to 27° C.). The mixture was then allowed to stir at room temperature and after 36 hours silica gel thin-layer chromatography (TLC) (1:1 ethyl acetate/hexanes) showed the reaction to be complete. The solvent was then removed in vacuo and the residual oil dissolved in 50 mL of ether. The solution was sequentially washed with 1.81 g of KOH in 20 mL of water, 0.6 g of KOH in 20 mL of water, and 20 mL of water, then dried ($Na_2SO_4$) and the solvent removed under reduced pressure to give 9.81 g (91%) of the N-butyldiazomalonate monoamide as a pale yellow oil.

To convert this to 1-(3-trifluoromethylphenyl)-3-carboethoxy-4-ethyl-2-pyrrolidone, a 300-mL three-necked round-bottomed flask equipped with a magnetic stirrer, heating mantle, thermometer, pressure-equalizing addition funnel, and reflux condenser carrying a nitrogen bubbler was charged with 190 mg of rhodium (II) acetate dimer and 150 mL of benzene. The suspension was stirred, heated to reflux, and a solution of 15.18 g (42.5 mmol) of the N-butyldiazomalonate monoamide in 50 mL of benzene was added dropwise over one hour. When the addition was complete the refluxing was continued for an additional hour, during which time the slow evolution of nitrogen ceased. The suspension was then allowed to cool to room temperature and filtered through diatomaceous earth to remove the rhodium catalyst. Removal of the solvent under reduced pressure provided a red oil that was purified by medium pressure liquid chromatography (MPLC) on silica gel using 30% ethyl acetate/hexanes as eluant. The yield was 6.89 g (49%) of the pyrrolidone ester as a very pale yellow oil.

As the next step in the procedure, this ester was converted to 1-(3-trifluoromethylphenyl)-3-chloro-3-carboethoxy-4-ethyl-2-pyrrolidone. To do this, a 300-mL round-bottomed flask equipped with a magnetic stirrer and nitrogen bubbler was charged with 6.89 g (20.9 mmol) of the ester and 150 mL of methylene chloride. The solution was stirred and 1.85 mL (3.10 g. 23.0 mmol) of sulfuryl chloride added all at once by pipette. After 14 hours at room temperature. GC analysis showed the reaction to be complete. The solution was washed with two 40-mL portions of water and 40 mL of saturated potassium carbonate solution, then dried ($Na_2SO_4$), and the solvent removed under reduced pressure to give 6.80 g (89%) of the converted ester as a thick, pale yellow oil.

The converted ester of the preceding paragraph was then further converted to the acid. 1-(3-trifluoromethylphenyl)-3-chloro-3-carboxy-4-ethyl-2-pyrrolidone, as follows. To a 250-mL boiling flask equipped with a magnetic stirrer was added 6.08 g (16.7 mmol) of the ester. 100 mL of ethanol, and 0.67 g (16.7 mmol) of NaOH in 5 mL of water. The mixture was stirred at room temperature and after two hours, silica gel TLC (1:1 ethyl acetate/hexanes) showed the reaction to be complete. The bulk of the ethanol was removed in vacuo and the residue taken up in 50 mL of water. The clear solution was washed with two 40-mL portions of ether, acidified with concentrated HCl, and extracted with three 40-mL portions of methylene chloride. The methylene chloride extracts were combined and dried ($MgSO_4$), and the solvent removed under reduced pressure to yield 4.96 g (88%) of the acid as a very pale yellow foam.

The acid was then converted to the final product. 1-(3-trifluoromethylphenyl)-3-chloro-3-carboxy-4-ethyl-2-pyrrolidone as follows. To a 100-mL boiling flask equipped with a nitrogen bubbler was added 4.33 g (12.9 mmol) of the acid. The flask was then heated with a heat gun which converted the foam to a mobile oil. Further heating effected the evolution of carbon dioxide as evidenced by vigorous bubble formation, When the gas evolution had ceased the flask and its contents were allowed to cool to room temperature affording 3.64 g (97%) of product as a thick oil that slowly solidified upon standing. Analysis by capillary GC showed this material to be a 54:44 trans/cis mixture of geometric isomers. The structure of the product was confirmed as that of 1-(3-trifluoromethylphenyl)-3-chloro-3-carboxy-4-ethyl-2-pyrrolidone by infrared spectroscopy (IR), mass spectrometry (MS) and nuclear magnetic resonance (NMR).

EXAMPLE 2

This example illustrates the preparation of 1-(3-trifluoromethylphenyl)-3-carbo-t-butoxy-4-ethyl-2-pyrrolidone in which, according to the above formula, m is 1 n is zero, $R^1$ is $CF_3$, $R^2$ is $COO-t-C_4H_9$, $R^3$ is $C_2H_5$, X and Y are both H, and Z is O. This compound is represented in Table I below as Compound No. 30.

The starting material for this compound was 1-(3-trifluoromethylphenyl)-3-carboxy-4-ethyl-2-pyrrolidone, prepared as described in Example 1. where it is an intermediate toward the final compound. To convert this ester to the acid the following procedure was used.

A 500-mL boiling flask equipped with a magnetic stirrer was charged with 14.00 g (42.5 mmol) of the ester and 150 mL of ethanol. The solution was stirred and 2.81 g (42.5 mmol) of 85% KOH in 10 mL of water was added all at once. The stirring was continued at room temperature overnight at which time the bulk of the ethanol was removed under reduced pressure. The residual syrup was dissolved in 250 mL of water and extracted with three 75-mL portions of methylene chloride. The aqueous layer was acidified with concentrated HCl and the extraction process repeated. The acidic extracts were combined and dried ($MgSO_4$), and the solvent removed under reduced pressure to provide 12.8 g (100%) of the acid as a colorless foam.

The acid was then converted to the t-butyl ester as follows. A 100-mL three-necked round-bottomed flask equipped with a magnetic stirrer, thermometer, and pressure equalizing addition funnel carrying a nitrogen bubbler was charged with 2.00 g (6.6 mmol) of carboxylic acid. 25 mL of benzene, and four drops of dimethylformamide (DMF). The solution was stirred and 0.62 mL (0.90 g. 7.1 mmol) of oxalyl chloride added all at once by pipette. When the evolution of gas had ceased the flask was immersed in an external ice bath and the contents cooled to 5° C. A solution of 0.50 g (6.8 mmol) of t-butanol and 0.56 g (7.1 mmol) of pyridine in 10 mL of benzene was added dropwise over 10 minutes. When the addition was complete the stirring was continued for 1.5 hours. At the end of this time the solution was washed with two 50-mL portions of water, then 50 mL of 3% aqueous HCl, then dried ($MgSO_4$). The solvent was removed under reduced pressure to afford 2.34 g (99%) of product as a very pale yellow oil. The structure was confirmed as that of 1-(3-trifluoromethylphenyl)-3-carbo-t-butoxy-4-ethyl-2-pyrrolidone by IR, MS and NMR.

These and further compounds prepared by similar procedures are listed in Table I below, together with physical data in the form of refractive indices or melting points where such measurements were possible, and physical descriptions where they were not.

The test procedures used are as follows:

Pre-Emergence Herbicidal Evaluation at 4 lb/acre

Planting flats were filled with sandy loam soil containing a fungicide and fertilizer. The soil was leveled and rows of grassy weeds, broadleaf weeds and yellow nutsedge (*Cyperus esculentus*), were planted thickly

TABLE I
COMPOUNDS

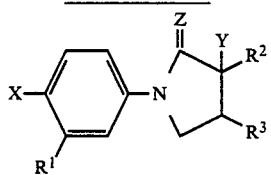

[In this table, Z is 0 except where otherwise indicated.]

| No. | $R^1$ | X | Y | $R^2$ | $R^3$ | $n_D^{30}$ or m.p. °C. |
|---|---|---|---|---|---|---|
| 1 | $CF_3$ | H | H | $COOC_2H_5$ | $C_2H_5$ | 1.5133 |
| 2 | $CF_3$ | H | Cl | $COOC_2H_5$ | $C_2H_5$ | thick syrup |
| 3 | $CF_3$ | H | Cl | COOH | $C_2H_5$ | thick syrup |
| 4 | $CF_3$ | H | H | Cl | $C_2H_5$ | 53–59 |
| 5 | $CF_3$ | F | H | $OC_2H_5$ | $C_2H_5$ | 1.5046 |
| 6 | $CF_3$ | F | Cl | $COOC_2H_5$ | $C_2H_5$ | thick syrup |
| 7 | $CF_3$ | F | Cl | COOH | $C_2H_5$ | thick syrup |
| 8 | $CF_3$ | F | H | Cl | $C_2H_5$ | waxy solid |
| 9 | [4-$CF_3$-6-Cl-pyrid-2-yloxy] | H | H | $COOC_2H_5$ | $C_2H_5$ | thick syrup |
| 10 | [4-$CF_3$-6-Cl-pyrid-2-yloxy] | H | Cl | $COOC_2H_5$ | $C_2H_5$ | thick syrup |
| 11 | [4-$CF_3$-6-Cl-pyrid-2-yloxy] | H | Cl | COOH | $C_2H_5$ | thick syrup |
| 12 | [4-$CF_3$-6-Cl-pyrid-2-yloxy] | H | H | Cl | $C_2H_5$ | thick syrup |
| 13 | $CF_3$ | H | H | COOH | $C_2H_5$ | thick syrup |
| 14 | $CF_3$ | H | H | CN | $C_2H_5$ | waxy solid |
| 15 | $CF_3$ | H | H | $COOC_2H_5$ | n-$C_3H_7$ | 1.5070 |
| 16 | $CF_3$ | H | H | Cl | $C_2H_5$ | 89–92 |
| | [Compound No. 16 is the pure trans-isomer of Compound No. 4, which is a 54:46 trans:cis mixture.] | | | | | |
| 17 | $CF_3$ | H | H | Cl | n-$C_3H_7$ | waxy solid |
| 18 | $CF_3$ | H | Cl | COOH | n-$C_3H_7$ | thick syrup |
| 19 | $CF_3$ | H | Cl | $COOC_2H_5$ | n-$C_3H_7$ | thick syrup |
| 20 | Cl | H | H | $COOC_2H_5$ | $C_2H_5$ | 1.5538 |
| 21 | Cl | H | Cl | $COOC_2H_5$ | | 1.5570 |
| 22 | Cl | H | Cl | COOH | $C_2H_5$ | thick syrup |
| 23 | Cl | H | H | Cl | $C_2H_5$ | waxy solid |
| 24 | $CF_3$ | H | Cl | Cl | $C_2H_5$ | waxy solid |
| 25 | H | H | H | Cl | $C_2H_5$ | 89–93.5 |
| 26 | CN | H | H | Cl | $C_2H_5$ | 74–85 |
| 27 | $CF_3$ | H | H | $COOC_2H_5$ | $CH=CH_2$ | 1.5126 |
| 28 | $CF_3$ | H | H | $COOC_2H_5$ | $C_2H_5$ | thick syrup |
| | [In Compound No. 28, Z = S] | | | | | |
| 29 | $CF_3$ | H | H | COO—CH($CH_3$)—$C_6H_5$ | $C_2H_5$ | 1.5220 |
| 30 | $CF_3$ | H | H | COO-t-$C_4H_9$ | $C_2H_5$ | 1.4829 |
| 31 | $CF_3$ | H | H | COO—C($CH_3$)$_2$—$C_2H_5$ | $C_2H_5$ | 1.4829 |
| 32 | $CF_3$ | H | H | COO—($CH_2$)$_2$—C($CH_3$)$_3$ | $C_2H_5$ | waxy solid |
| 33 | $CF_3$ | H | H | COO—CH($CH_3$)—$C_3H_5$ | $C_2H_5$ | 1.4811 |
| 34 | $CF_3$ | H | H | $COOCH_2$—C($C_2H_4$*)—$CH_3$ | $C_2H_5$ | 56–65 |
| 35 | $CF_3$ | H | H | COO-t-$C_4H_9$ | $C_2H_5$ | waxy solid |
| 36 | $CF_3$ | H | H | COO—C($CH_3$)$_2$—CHCl | $C_2H_5$ | thick syrup |
| 37 | $CF_3$ | H | H | COO—C($CH_3$)$_2$—$CF_3$ | $C_2H_5$ | 1.4641 |

[* in Compound Nos. 33 and 34 denotes cyclopropyl ring.]

The compounds listed in the foregoing table were tested for herbicidal activity by various methods and at various rates of application. The results of some of these tests are given below. As one skilled in the art is aware, the results obtained in herbicidal screening tests are affected by a number of factors that are not readily controllable. Environmental conditions such as amount of sunlight and water, soil type, soil pH, temperature and humidity, are examples of such factors. The depth of planting and the application rate of the herbicide, as well as the nature of crops being tested, can also affect the test results. Results will also vary from crop to crop and within the crop varieties.

enough so that several seedlings emerged per inch of row. The grassy weeds were yellow foxtail (*Setaria viridis*), watergrass (*Echinochloa crusgalli*) and wild oat (*Avena fatua*). Broadleaf weeds utilized were annual morningglory (*Ipomoea purpurea*). velvetleaf (*Abutilon theophrasti*), wild mustard (*Brassica kaber*), and curly dock (*Rumex crispus*).

Solutions of the test compounds were made by weighing out 333 mg of the test compound into a 60-mL wide-mouth bottle, then dissolving the compound in 25 mL of acetone containing 1% Tweene ® 20 (polyoxyethylene sorbitan monolaurate emulsifier). Additional solvents, not exceeding 5 mL, were used if needed to dissolve the compound. A 20.5-mL aliquot was then taken from the solution and diluted with 25 mL of an acetone:water mixture (19:1) containing 1% Tweene ® 20. This was used as the spray solution.

One day after planting, the flats were sprayed with the spray solution at a rate of 80 gallons of solution per acre with the compound being applied at a rate of 4 pounds per acre (4.48 kg/hectare).

The flats were then returned to the greenhouse and watered daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill; a dash indicates that no test was performed at that level of application.

Post-Emergence Herbicidal Evaluation at 4 lb/acre

The soil was prepared and seeded with the same varieties used in the pre-emergence test. The flats were placed in the greenhouse at 70°–85° F. (21°–29° C.) and watered by sprinkling. Twelve to fourteen days after planting, the flats were sprayed at a rate of 80 gallons of solution per acre. Each compound was applied at the rate of 4 pounds/acre (4.48 kg/hectare). using a spray solution prepared as in the pre-emergence test.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the same basis as for the pre-emergence evaluation.

The following table lists the results of these tests, in terms of averages for the grasses and broadleaf weeds, with yellow nutsedge listed separately, in both pre- and post-emergence evaluations.

TABLE II

HERBICIDE TEST RESULTS - PERCENT CONTROL AT 4 LB/ACRE

| Compound No. | Pre-Emergence | | | Post-Emergence | | |
|---|---|---|---|---|---|---|
| | YNS | AVG | AVB | YNS | AVG | AVB |
| 1 | 0 | 63 | 25 | 0 | 37 | 38 |
| 2 | 0 | 65 | 20 | 0 | 28 | 34 |
| 3 | 0 | 65 | 53 | 0 | 37 | 46 |
| 4 | — | — | — | — | — | — |
| 5 | 0 | 62 | 31 | — | 23 | 51 |
| 6 | 0 | 40 | 21 | — | 27 | 66 |
| 7 | 0 | 60 | 58 | 0 | 35 | 84 |
| 8 | — | — | — | — | — | — |
| 9 | 0 | 50 | 59 | 0 | 0 | 59 |
| 10 | 0 | 17 | 28 | 0 | 0 | 51 |
| 11 | 0 | 30 | 28 | 0 | 13 | 61 |
| 12 | 30 | 70 | 65 | 0 | 37 | 48 |
| 13 | 0 | 17 | 9 | 0 | 0 | 29 |
| 14 | 0 | 43 | 36 | 0 | 28 | 40 |
| 15 | 0 | 45 | 12 | 0 | 15 | 30 |
| 16 | 90 | 97 | 100 | 75 | 68 | 60 |
| 17 | 0 | 80 | 73 | 0 | 50 | 63 |
| 18 | 0 | 0 | 0 | 0 | 0 | 57 |
| 19 | 0 | 0 | 0 | 0 | 0 | 42 |
| 20 | 0 | 13 | 17 | 0 | 2 | 25 |
| 21 | 0 | 47 | 5 | 0 | 0 | 35 |
| 22 | 0 | 20 | 38 | 0 | 2 | 37 |
| 23 | — | — | — | — | — | — |
| 24 | — | — | — | — | — | — |
| 25 | 70 | 95 | 97 | 50 | 67 | 53 |
| 26 | 80 | 97 | 99 | 80 | 88 | 80 |
| 27 | 0 | 35 | 40 | 0 | 27 | 37 |
| 28 | 0 | 53 | 47 | 0 | 40 | 60 |
| 29 | 0 | 33 | 33 | 0 | 40 | 50 |
| 30 | 0 | 97 | 80 | 0 | 78 | 83 |
| 31 | 0 | 53 | 47 | 0 | 0 | 57 |
| 32 | 0 | 33 | 23 | 0 | 0 | 70 |
| 33 | 0 | 63 | 73 | 0 | 40 | 87 |
| 34 | 0 | 57 | 50 | 0 | 7 | 37 |
| 35 | 0 | 67 | 40 | 0 | 30 | 87 |
| 36 | 0 | 60 | 40 | 0 | 33 | 63 |
| 37 | 0 | 63 | 53 | 0 | 40 | 53 |

Abbreviations:
YNS: Yellow Nutsedge
AVG: Grasses averaged
AVB: Broadleaf weeds averaged Herbicidal and Crop Injury Tests at 0.25–2.0 lb/acre Pre-emergence and post-emergence tests were performed at application rates ranging from 0.10 to 2.00 lb/acre based on the active ingredient (0.112 to 2.24 kg/hectare) for a number of the compounds listed in Table I. This round of testing extended to both weed and crop species, and followed the same general procedure as the 4 lb/acre tests, except for the plant species used. The species were as follows:

| | | |
|---|---|---|
| Grass weeds: | yellow foxtail | *Setaria viridis* |
| | annual ryegrass | *Lolium multiflorum* |
| | watergrass | *Echinochloa crusgalli* |
| | shattercane | *Sorghum bicolor* |
| | wild oat | *Avena fatua* |
| | broadleaf signalgrass | *Brachiaria platyphylla* |
| | downy brome | *Bromus tectorum* |
| Broadleaf weeds: | annual morningglory | *Ipomoea purpurea* |
| | cocklebur | *Xanthium pensylvanicum* |
| | sesbania | *Sesbania exasperata* |
| | velvetleaf | *Abutilon theophrasti* |
| | sicklepod | *Cassia obtusifolia* |
| | wild mustard | *Brassica kaber* |
| Other: | yellow nutsedge | *Cyperus esculentus* |
| Crops: | cotton | *Gossypium herbaceum* |
| | soybean | *Glycine max* |
| | corn | *Zea mays* |
| | milo | *Sorghum vulgare* |
| | wheat | *Triticum aestivum* |
| | rice | *Oryza sativa* |
| | sugarbeet | *Beta vulgaris* |

The results of these test are listed in Table III, in which the indicia used are the same as those in Table II.

TABLE III

HERBICIDE AND CROP INJURY TEST RESULTS
PERCENT CONTROL AT 2 LB/ACRE AND LESS

| Rate | Crops* | | | | | | | Weeds | | |
|---|---|---|---|---|---|---|---|---|---|---|
| | (1) | (2) | (3) | (4) | (5) | (6) | (7) | YNS | AVG | AVB |
| Compound No. 4 - Pre-Emergence: | | | | | | | | | | |
| 1.00 | 90 | 85 | 100 | 70 | 100 | 90 | 45 | 40 | 100 | 100 |
| 0.50 | 90 | 85 | 100 | 70 | 100 | 90 | 50 | 40 | 100 | 100 |
| 0.25 | 70 | 60 | 100 | 30 | 100 | 80 | 20 | 25 | 99 | 90 |
| Compound No. 4 - Post-Emergence: | | | | | | | | | | |
| 1.00 | 100 | 25 | 80 | 45 | 40 | 55 | 60 | 55 | 51 | 85 |
| 0.50 | 100 | 40 | 70 | 55 | 30 | 60 | 40 | 65 | 51 | 80 |
| 0.25 | 100 | 10 | 25 | 15 | 40 | 20 | 30 | 30 | 39 | 65 |
| Compound No. 8 - Pre-Emergence: | | | | | | | | | | |
| 1.00 | 95 | 99 | 98 | 100 | 100 | 65 | 100 | 75 | 98 | 99 |
| 0.50 | 95 | 65 | 90 | 75 | 100 | 40 | 10 | 60 | 95 | 78 |
| 0.25 | 80 | 30 | 90 | 40 | 100 | 10 | 10 | 0 | 81 | 72 |
| 0.10 | 60 | 10 | 65 | 10 | 100 | 15 | 0 | 0 | 70 | 54 |
| Compound No. 23 - Pre-Emergence: | | | | | | | | | | |
| 1.00 | 70 | 25 | 50 | 40 | 100 | 45 | 100 | — | 77 | 42 |
| 0.50 | 35 | 0 | 50 | 40 | 90 | 40 | 30 | — | 62 | 38 |
| 0.25 | 10 | 0 | 20 | 30 | 50 | 20 | 25 | 0 | 47 | 15 |
| 0.13 | 0 | 0 | 0 | 30 | 40 | 25 | 100 | 0 | 21 | 6 |
| Compound No. 23 - Post-Emergence: | | | | | | | | | | |
| 2.00 | 90 | 35 | 35 | 40 | 90 | 25 | 0 | 0 | 71 | 72 |
| 1.00 | 40 | 0 | 25 | 15 | 0 | 0 | 35 | 0 | 33 | 39 |
| Compound No. 24 - Pre-Emergence: | | | | | | | | | | |
| 1.00 | 75 | 100 | 25 | 30 | 100 | 45 | 15 | 20 | 89 | 95 |
| 0.50 | 30 | 95 | 10 | 10 | 100 | 30 | 0 | 0 | 81 | 62 |
| 0.25 | 20 | 75 | 0 | 0 | 100 | 0 | 0 | 0 | 68 | 61 |
| 0.13 | 30 | 10 | 0 | 0 | 100 | 30 | 0 | 0 | 62 | 36 |
| Compound No. 24 - Post-Emergence: | | | | | | | | | | |
| 1.00 | 50 | 25 | 40 | 0 | 100 | 35 | 30 | 10 | 78 | 99 |
| 0.50 | 95 | 0 | 15 | 0 | 100 | 0 | 10 | 0 | 44 | 61 |

*Crops: Crops:
(1) Soybean
(2) Wheat
(3) Milo
(4) Rice
(5) Sugarbeet
(6) Corn
(7) Cotton The compounds of the present invention are useful as herbicides and can be applied in a variety of ways known to those skilled in the art, at various concentrations. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene or other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated napthalenes, xylene and other organic solvents. Pressurized sprays, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

The compounds of the present invention are also useful when combined with other herbicides and/or defoliants, dessicants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, dessicants and plant growth inhibitors with which the compounds of this invention can be combined are:

chlorophenoxy herbicides such as 2,4-D, 2,4,5-T, MCPA, MCPB, 2,4-DB, 2,4-DEB, 4-CPA, 2,4,5-TB, and silvex;

carbamate herbicides such as propham, chlorpropham, swep, and barban;

thiocarbamate and dithiocarbamate herbicides such as CDEC, metham-sodium, EPTC, diallate, PEBC, and vernolate;

substituted urea herbicides such as norea, dichloral urea, chloroxuron, cycluron, fenuron, monuron, monuron TCA, diuron, linuron, monolinuron neburon, buturon and trimeturon;

symmetrical triazine herbicides such as simazine, chlorazine, desmetryne, norazine, ipazine, prometryn, atrazine, trietazine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorophenylacetic acid, 3-methoxy-2,6-dichlorophenylacetic acid, 2-methoxy-3,5,6-trichlorphenylacetic acid and 2,4-dichloro-3-nitrobenzoic acid;

and such compounds as aminotriazole, maleic hydrazide, phenylmercury acetate, endothal, technical chlordane, DCPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichloro-phenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, sesone, terbacil, terbutol, TCBA, alachlor, nitralin, sodium tetraborate, calcium cyanamide, S,S,S-tributylphosphorotrithioate and propanil.

These formulations can be applied to the areas where control is desired by conventional methods. Dust and liquid compositions, for example, can be applied by the use of power-dusters, boom and hand sprayers and spray dusters, The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations, The following are examples of typical formulations,

| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size,

| 5% granules: | |
| | 5 parts active compound |
| | 0.25 part epichlorohydrin |
| | 0.25 part cetyl polyglycol ether |
| | 3.5 parts polyethylene glycol |
| | 91 parts kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

| | wettable powders |
| --- | --- |
| 70%: | 70 parts active compound |
| | 5 parts sodium dibutylnaphthylsulfonate |
| | 3 parts naphthalenesulfonic acid/phenolsulfonic acid/formaldehyde condensate (3:2:1) |

| wettable powders | | |
|---|---|---|
| | 10 | parts kaolin |
| | 12 | parts Champagne chalk |
| 40%: | 40 | parts active compound |
| | 5 | parts sodium lignin sulfonate |
| | 1 | part sodium dibutylnaphthalenesulfonic acid |
| | 54 | parts silicic acid |
| 25%: | 25 | parts active compound |
| | 4.5 | parts calcium lignin sulfate |
| | 1.9 | parts Champagne chalk/hydroxyethyl cellulose (1:1) |
| | 1.5 | parts sodium dibutylnaphthalenesulfonate |
| | 19.5 | parts silicic acid |
| | 19.5 | parts Champagne chalk |
| | 28.1 | parts kaolin |
| 25%: | 25 | parts active compound |
| | 2.5 | parts isooctylphenoxy-polyethylene-ethanol |
| | 1.7 | parts Champagne chalk/hydroxyethyl cellulose (1:1) |
| | 8.3 | parts sodium aluminum silicate |
| | 16.5 | parts kieselguhr |
| | 46 | parts kaolin |
| 10%: | 10 | parts active compound |
| | 3 | parts of a mixture of sodium salts of saturated fatty alcohol sulfates |
| | 5 | parts naphthalenesulfonic acid/formaldehyde condensate |
| | 82 | parts kaolin |

These wettable powders are prepared by intimately mixing the active compounds with the additive in suitable mixers, and grinding the resulting mixtures in mills or rollers.

| 25% emulsifiable concentrate: | |
|---|---|
| 25 | parts active substance |
| 2.5 | parts epoxidized vegetable oil |
| 10 | parts of an alkylarylsulfonate/fatty alcohol polyglycol ether mixture |
| 5 | parts dimethylformamide |
| 57.5 | parts xylene |

What is claimed is:
1. A compound having the formula

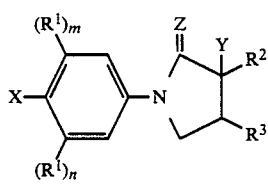

in which:
 $R^1$ is a member selected from the group consisting of halogen, trifluoromethyl, cyano, $CH_3$, $CF_2CHF_2$, $OCF_2CHF_2$, $OCHF_2$, $OCF_3$, $SCH_3$, $S(O)CH_3$, $SO_2CH_3$, methoxyiminomethyl, methoxyimino-1-ethyl, benzoyloxyiminomethyl, benzoyloxyimino-1-ethyl, pyridyloxy, and pyridyloxy substituted with one or more members of the group consisting of halogen and trifluoromethyl;
 $R^2$ is a member selected from the group consisting of halogen, cyano, carboxy, carbalkoxy containing an alkyl group of 1 to 8 carbon atoms, and carbalkoxy containing an alkyl group of 1 to 8 carbon atoms substituted with a member selected from the group consisting of halogen, trifluoromethyl and phenyl;
 $R^3$ is a member selected from the group consisting of $C_1$–$C_4$ alkyl and $C_2$–$C_4$ alkenyl;
 X is a member selected from the group consisting of H and halogen;
 Y is a member selected from the group consisting of H and halogen;
 Z is a member selected from the group consisting of O and S; and
 m and n are independently zero or 1.

2. A compound according to claim 1 in which m is 1 and n is zero.

3. A compound according to claim 1 in which m is 1 and n is zero, and $R^1$ is a member selected from the group consisting of halogen, trifluoromethyl, cyano, and pyridyloxy substituted with one or more members of the group consisting of halogen and trifluoromethyl.

4. A compound according to claim 1 in which m is 1 and n is zero, and $R^1$ is a member selected from the group consisting of chloro, trifluoromethyl, cyano, and pyrid-2-yloxy substituted with one or more members of the group consisting of halogen and trifluoromethyl.

5. A compound according to claim 1 in which m is 1 and n is zero. $R^1$ is trifluoromethyl, and X is a member selected from the group consisting of H and fluoro.

6. A compound according to claim 1 in which m is 1 and n is zero, $R^1$ is trifluoromethyl, and X is a member selected from the group consisting of H and fluoro.

7. A compound according to claim 1 in which $R^2$ is a member selected from the group consisting of halogen, carboxy, and carbalkoxy containing an alkyl group of from 1 to 4 carbon atoms.

8. A compound according to claim 1 in which $R^2$ is a member selected from the group consisting of chloro, carboxy and carbethoxy.

9. A compound according to claim 1 in which $R^2$ is chloro.

10. A compound according to claim 1 in which $R^3$ is a member selected from the group consisting of ethyl and vinyl.

11. A compound according to claim 1 in which $R^3$ is $C^1$–$C^4$ alkyl.

12. A compound according to claim 1 in which $R^3$ is ethyl.

13. A compound according to claim 1 in which Y is a member selected from the group consisting of H and chloro.

14. A compound according to claim 1 in which Y is H.

15. A compound according to claim 1 in which Z is O.

16. A compound according to claim 1 in which m is 1, n is zero, $R^1$ is trifluoromethyl, $R^2$ is chloro, $R^3$ is ethyl, X is H, Y is H, and Z is O.

17. A compound according to claim 1 in which m is 1, n is zero, $R^1$ is trifluoromethyl, $R^2$ is chloro, $R^3$ is ethyl, X is fluoro, Y is H, and Z is O.

18. A compound according to claim 1 in which m is 1. n is zero, $R^1$ is trifluoromethyl, $R^2$ is chloro, $R^3$ is ethyl, X is H, Y is H, and Z is O.

19. An herbicidal composition comprising:
 (a) an herbicidally effective amount of a compound having the formula

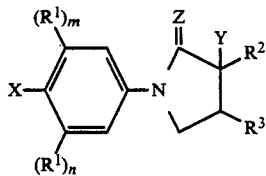

in which:
R¹ is a member selected from the group consisting of halogen, trifluoromethyl, cyano, $CH_3$, $CF_2CHF_2$, $OCF_2CHF_2$, $OCHF_2$, $OCF_3$, $SCH_3$, $S(O)CH_3$, $SO_2CH_3$, methoxyiminomethyl, methoxyimino-1-ethyl, benzoyloxyiminomethyl, benzoyloxyimino-1-ethyl, pyridyloxy, and pyridyloxy substituted with one or more members of the group consisting of halogen and trifluoromethyl;

R² is a member selected from the group consisting of halogen, cyano, carboxy, carbalkoxy containing an alkyl group of 1 to 8 carbon atoms, and carbalkoxy containing an alkyl group of 1 to 8 carbon atoms substituted with a member selected from the group consisting of halogen, trifluoromethyl and phenyl;

R³ is a member selected from the group consisting of $C_1$–$C_4$ alkyl and $C_2$–$C_4$ alkenyl;

X is a member selected from the group consisting of H and halogen;

Y is a member selected from the group consisting of H and halogen;

Z is a member selected from the group consisting of O and S; and m and n are independently zero or 1; and (b) an herbicidally suitable inert diluent or carrier.

20. An herbicidal composition according to claim 19 in which m is 1 and n is zero.

21. An herbicidal composition according to claim 19 in which m is 1 and n is zero, and R¹ is a member selected from the group consisting of halogen, trifluoromethyl, cyano, and pyridyloxy substituted with one or more members of the group consisting of halogen and trifluoromethyl.

22. An herbicidal composition according to claim 19 in which m is 1 and n is zero, and R¹ is a member selected from the group consisting of chloro, trifluoromethyl, cyano, and pyrid-2-yloxy substituted with one or more members of the group consisting of halogen and trifluoromethyl.

23. An herbicidal composition according to claim 19 in Which m is 1 and n is zero. R¹ is trifluoromethyl, and X is a member selected from the group consisting of H and fluoro.

24. An herbicidal composition according to claim 19 in which m is 1 and n is zero, R¹ is trifluoromethyl, and X is a member selected from the group consisting of H and fluoro.

25. An herbicidal composition according to claim 19 in which R² is a member selected from the group consisting of halogen, carboxy, and carbalkoxy containing an alkyl group of from 1 to 4 carbon atoms.

26. An herbicidal composition according to claim 19 in which R² is a member selected from the group consisting of chloro, carboxy and carbethoxy.

27. An herbicidal composition according to claim 19 in which R² is chloro.

28. An herbicidal composition according to claim 19 in which R³ is a member selected from the group consisting of ethyl and Vinyl.

29. An herbicidal composition according to claim 19 in which R³ is $C^1$–$C^4$ alkyl.

30. An herbicidal composition according to claim 19 in which R³ is ethyl.

31. An herbicidal composition according to claim 19 in which Y is a member selected from the group consisting of H and chloro.

32. An herbicidal composition according to claim 19 in which Y is H.

33. An herbicidal composition according to claim 19 in which Z is O.

34. An herbicidal composition according to claim 19 in which m is 1. n is zero. R¹ is trifluoromethyl, R² is chloro, R³ is ethyl, X is H, Y is H, and Z is O.

35. An herbicidal composition according to claim 19 in which m is 1, n is zero, R¹ is trifluoromethyl, R² is chloro. R³ is ethyl, X is fluoro, Y is H. and Z is O.

36. An herbicidal composition according to claim 19 in which m is 1, n is zero. R¹ is trifluoromethyl, R² is chloro, R³ is ethyl, X is H, Y is H, and Z is O.

37. A method of controlling undesirable vegetation comprising applying to said vegetation or to the locus thereof an herbicidally effective amount of a compound having the formula

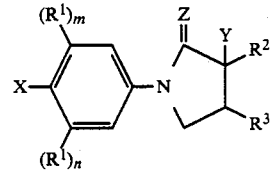

in which:
R¹ is a member selected from the group consisting of halogen, trifluoromethyl, cyano, $CH_3$, $CF_2CHF_2$, $OCF_2CHF_2$, $OCHF_2$, $OCF_3$, $SCH_3$, $S(O)CH_3$, $SO_2CH_3$, methoxyiminomethyl, methoxyimino-1-ethyl, benzoyloxyiminomethyl, benzoyloxyimino-1-ethyl, pyridyloxy, and pyridyloxy substituted with one or more members of the group consisting of halogen and trifluoromethyl;

R² is a member selected from the group consisting of halogen, cyano, carboxy, carbalkoxy containing an alkyl group of 1 to 8 carbon atoms, and carbalkoxy containing an alkyl group of 1 to 8 carbon atoms substituted with a member selected from the group consisting of halogen, trifluoromethyl and phenyl;

R³ is a member selected from the group consisting of $C_1$–$C_4$ alkyl and $C_2$–$C_4$ alkenyl;

X is a member selected from the group consisting of H and halogen;

Y is a member selected from the group consisting of H and halogen;

Z is a member selected from the group consisting of O and S; and m and n are independently zero or 1.

38. A method according to claim 37 in which m is 1 and n is zero.

39. A method according to claim 37 in which m is 1 and n zero and R¹ is a member selected from the group consisting of halogen, trifluoromethyl cyano, and pyridyloxy substituted with one or more members of the group consisting of halogen and trifluoromethyl.

40. A method according to claim 37 in which m is 1 and n is zero, and $R^1$ is a member selected from the group consisting of chloro, trifluoromethyl, cyano, and pyrid-2-yloxy substituted with one or more members of the group consisting of halogen and trifluoromethyl.

41. A method according to claim 37 in which m is 1 and n is zero, $R^1$ is trifluoromethyl, and X is a member selected from the group consisting of H and fluoro.

42. A method according to claim 37 in which m is 1 and n is zero, $R^1$ is trifluoromethyl, and X is a member selected from the group consisting of H and fluoro.

43. A method according to claim 37 in which $R^2$ is a member selected from the group consisting of halogen, carboxy, and carbalkoxy containing an alkyl group of from 1 to 4 carbon atoms.

44. A method according to claim 37 in which $R^2$ is a member selected from the group consisting of chloro, carboxy and carbethoxy.

45. A method according to claim 37 in which $R^2$ is chloro.

46. A method according to claim 37 in which $R^3$ is a member selected from the group consisting of ethyl and vinyl.

47. A method according to claim 37 in which $R^3$ is $C^1$-$C^4$ alkyl.

48. A method according to claim 37 in which $R^3$ is ethyl.

49. A method according to claim 37 in which Y is a member selected from the group consisting of H and chloro.

50. A method according to claim 37 in which Y is H.

51. A method according to claim 37 in which Z is O.

52. A method according to claim 37 in which m is 1, n is zero, $R^1$ is trifluoromethyl, $R^2$ is chloro, $R^3$ is ethyl, X is H, Y is H, and Z is O.

53. A method according to claim 37 in which m is 1, n is zero, $R^1$ is trifluoromethyl, $R^2$ is chloro, $R^3$ is ethyl, X is fluoro, Y is H, and Z is O.

54. A method according to claim 37 in which m is 1, n is zero, $R^1$ is trifluoromethyl, $R^2$ is chloro, $R^3$ is ethyl, X is H, Y is H, and Z is O.

* * * * *